United States Patent [19]

Kimura et al.

[11] Patent Number: 4,470,928

[45] Date of Patent: Sep. 11, 1984

[54] PROCESS FOR PRODUCING CYANOVALERIC ESTERS AND CAPROLACTAM

[75] Inventors: Kohji Kimura; Toshiro Isoya, both of Nobeoka, Japan

[73] Assignee: Asahi Kasei Kogyo Kabushiki Kaisha, Osaka, Japan

[21] Appl. No.: 420,883

[22] Filed: Sep. 21, 1982

[30] Foreign Application Priority Data

Oct. 15, 1981 [JP] Japan .................................. 164567
Dec. 4, 1981 [JP] Japan .................................. 194376

[51] Int. Cl.$^3$ .................. C07D 223/10; C07C 120/00; C07C 121/407; C07C 121/16
[52] U.S. Cl. ............................ 260/239.3 A; 260/465.4
[58] Field of Search ....................... 260/465.4, 239.3 A

[56] References Cited

U.S. PATENT DOCUMENTS

| | | | |
|---|---|---|---|
| 2,322,273 | 6/1943 | Biggs | 260/465.4 |
| 2,377,795 | 6/1945 | Loder | 260/465.8 R |
| 2,970,997 | 2/1961 | Fischer et al. | 260/239.3 A |
| 3,050,547 | 8/1962 | Waters | 260/404 X |
| 3,341,567 | 9/1967 | Yasui et al. | 260/465.8 R |
| 3,706,779 | 12/1972 | Nabeta et al. | 260/464 |
| 3,919,197 | 11/1975 | Garritsen et al. | 260/239.3 A |
| 3,931,292 | 1/1976 | Garritsen et al. | 260/239.3 A X |
| 3,988,319 | 10/1976 | Mares | 260/239.3 A |

OTHER PUBLICATIONS

Zhur. Obshchei Khim., 29, 3350, (1959), pp. 3312-3316; Zil'berman.
Ind. Eng. Chem., Process Des. Dev., 17, 9 (1978), pp. 9-16; Mares et al.

*Primary Examiner*—Joseph Paul Brust
*Attorney, Agent, or Firm*—Armstrong, Nikaido, Marmelstein & Kubovcik

[57] ABSTRACT

Caprolactam can be produced with an economical advantage without formation of by-products in a high yield by subjecting adipic acid and adiponitrile to interchange reaction at an elevated temperature, adding an alcohol directly to the interchange reaction mixture without isolating the resulting cyanovaleric acid to esterify the cyanovaleric acid with said alcohol into a cyanovaleric ester, reducing the cyanovaleric ester with a catalyst into an aminocaproic ester, heating the aminocaproic ester in a polyhydric alcohol having a higher boiling point than that of caprolactam to convert the ester into caprolactam, isolating the caprolactam by distillation and recycling the liquid distillation residue to the system for heating said polyhydric alcohol and said aminocaproic ester.

12 Claims, 2 Drawing Figures

FIG. 1

PROCESS FOR PRODUCING CYANOVALERIC ESTERS AND CAPROLACTAM

This invention relates to a process for producing caprolactam without forming ammonium sulfate, as by-product, at all. More particularly, this invention relates to a process for producing caprolactam from adipic acid and adiponitrile as starting materials which forms substantially no by-products.

For the industrial production of caprolactam, the process which comprises oximating cyclohexanone with hydroxylamine and then subjecting the resulting cyclohexanone oxime to Beckmann rearrangement to obtain caprolactam has hitherto been used most extensively. This process, however, has the serious fault that the formation of ammonium sulfate, as by-product, cannot be avoided in all the steps of the production of hydroxylamine, the oximation and the Beckmann rearrangement. For this reason, various technical improvements have all aimed at suppressing the formation of ammonium sulfate as by-product. For example, the production of hydroxylamine by the formation of ammonium sulfate as by-product has been considerably inhibited by replacing the Roschig method of producing hydroxylamine which comprises reducing ammonium nitrate with $SO_2$ and then hydrolyzing the reduced product by a method which comprises reducing $NO_3^-$ with hydrogen in a phosphate buffer solution, or by substituting direct extraction of caprolactam with alkylphenol from the caprolactam-containing sulfuric acid solution formed by the Beckmann rearrangement for the neutralization of said caprolactam-containing sulfuric acid solution with $NH_3$ followed by extracting caprolactam with a solvent from the neutralization product. However, the fault that ammonium sulfate is formed as a by-product still remains, so that development of novel process for the production of caprolactam free from formation of by-products has been awaited.

As one of such processes, there is a process which comprises acetylating cyclohexanone with a ketene/acetic anhydride mixture into cyclohexenyl acetate, subsequently nitrating the latter to obtain nitrocyclohexanone with liberation of acetic acid, then hydrolyzing the nitrocyclohexanone, reducing the hydrolyzate into aminocyclohexanone and heating the latter in an aqueous solvent to obtain caprolactam (Japanese patent publication No. 8,542/72). In this process, the ketene for acetylating cyclohexanone can be regenerated from acetic acid and reused. However, the regeneration cost is very high. Furthermore, there is no appropriate solvent capable of effectively extracting caprolactam from an aqueous solution thereof, so that the removal of the extracting solvent by distillation for isolating the caprolactam necessitates an enormous utility cost. Therefore, this process cannot be said to be economically excellent and it has not yet been industrialized.

As another process, there is a process which comprises reducing cyanovaleric acid or a cyanovaleric ester into aminocaproic acid or an aminocaproic ester followed by cyclizing the aminocaproic acid or ester to obtain caprolactam. However, this process is impractical because the method of producing the cyanovaleric acid or ester and the method of cyclizing the same into caprolactam have many problems.

That is, the process for the industrial production of cyanovaleric acid or cyanovaleric ester has not yet been established. Though cyanovaleric acid can be produced from adipic acid on the laboratory scale by applying the method of preparing cyanopelargonic acid (Org. Synth., III, 768), the yield is so low that the process cannot be put into practice. Moreover, though the production of cyanovaleric acid or a cyanovaleric ester by the oxo reaction of pentenonitrile is also known (Japanese patent application (Laid-Open) No. 36,625/77), it cannot be said to be practical because of low yield.

A further process for producing cyanovaleric acid uses a reaction between adipic acid and a cyanide (hereinafter referred to as interchange reaction) (Zhur. Obshchei Khim. 29, 3350 (1959) and Japanese patent application Kokai (Laid-Open) No. 47,927/75). However, when the reaction time is prolonged or the amount of the cyanide is increased with the aim of enhancing the conversion of adipic acid, the yield of cyanovaleric acid decreases and, instead thereof, adiponitrile becomes the main product. Furthermore, when adipic acid and adiponitrile are subjected to interchange reaction, a sufficiently high yield of cyanovaleric acid cannot be achieved.

A further problem of this technique consists in the low conversion of the cyanide into a carboxylic acid in the interchange reaction thereof with adipic acid. As to the production of adiponitrile from adipic acid by interchange reaction, U.S. Pat. No. 2,377,795 and Ann. Chem. 716, 78 (1968) do not state the conversion of the cyanide into a carboxylic acid though they state the yield of adponitrile based on adipic acid. The present inventors have conducted an experiment on adipic acid and acetonitrile for the purpose of ascertaining this point to reveal that the yield of acetic acid is only about 50% of theoretical value and amides are formed in addition to it. The amides are sublimable, so that they make it quite difficult to separate and purify the product.

There has been studied an improved technique for the interchange reaction between adipic acid and a cyanide (Japanese patent publication No. 13,201/68 and J. Org. Chem. 36, 3050 (1971)). However, clearly, such an improved technique is not suitable for the production of cyanovaleric acid, even though it contributes to an improvement of yield of dinitrile.

The problem in a process for cyclizing aminocaproic acid or an aminocaproic ester into caprolactam is that the concentration of the aminocaproic acid or ester must be kept at a low level in the step of cyclization in order to suppress the formation of polymer. That is, in the process for producing caprolactam by heating aminocaproic acid or an aminocaproic ester in water or an organic solvent (Japanese patent publications Nos. 9,473/74; 6,112/55; and 14,563/63, Japanese patent application Kokai (Laid-Open) No. 43780/76 and Ind. Eng. Chem. Process Des. Dev., 17, 9 (1978)), when the aminocaproic acid is, for example, heated in a water solvent at a low concentration caprolactam is obtained as a dilute aqueous solution. Therefore, in order to isolate the caprolactam, it is necessary to remove a large amount of water or to extract the caprolactam with an extracting solvent such as chloroform, benzene or the like. However, the utility cost necessary for removing the water or extracting solvent is tremendous. Even if an organic solvent is used, the utility cost is still high and the yield is unsatisfactory.

The present inventors have discovered a process for producing caprolactam from inexpensive starting materials without forming by-products by which process such disadvantages have been overcome. That is, it has been discovered that caprolactam can be obtained without forming by-products by using, as starting material, adipic acid and adiponitrile which are both obtained at low cost as the starting precursors of Nylon 6,6.

According to this invention, there is provided a process for producing caprolactam in a high yield without forming by-product which comprises subjecting adipic acid and adiponitrile to interchange reaction at an elevated temperature, adding an alcohol directly to the interchange reaction mixture without isolating cyanovaleric acid which is the product of the interchange raction, to esterify the cyanovaleric acid with said alcohol to obtain a cyanovaleric ester, reducing the cyanovaleric ester by the use of a catalyst to obtain an aminocaproic ester, heating the aminocaproic ester in a polyhydric alcohol having a higher boiling point than that of caprolactam to convert the ester into caprolactam, isolating the resulting caprolactam by distillation, and recycling the liquid distillation residue to the system for heating said polyhydric alcohol and said aminocaproic ester.

This invention will be explained in more detail with reference to the accompanying drawings, wherein.

In the process of this invention, caprolactam can be produced with an economical advantage without formation of by-products by carrying out the following three steps: Thus, the first step is to produce a cyanovaleric ester by heating and subjecting adipic acid and adiponitrile to interchange reaction, directly adding an alcohol to the interchange reaction mixture without isolating the cyanovaleric acid, which is the interchange reaction product, from the reaction mixture, and heating the resulting mixture to esterify the cyanovaleric acid. The second step is to produce an aminocaproic ester by reducing the cyanovaleric ester obtained in the first step in the presence of a catalyst and in the presence or absence of a solvent. The third step is to produce caprolactam by heating the aminocaproic ester obtained in the second step in a polyhydric alcohol (solvent) having a boiling point higher than that of caprolactam, separating the resulting caprolactam by distillation, which includes recycling the liquid distillation residue containing the substances which have not yet been converted into caprolactam (said substances include aminocaprolactam-converted product and caprolactam oligomer, and hereinafter they are referred to as the unconverted substances) to the system for heating the aminocaproic acid, thereby producing caprolactam from the unconverted substances and aminocaproic ester.

The details of the production of a cyanovaleric ester in the first step by subjecting adipic acid and adiponitrile to interchange reaction, esterifying the reaction product with an alcohol are as follows:

In the interchange reaction between adipic acid and adiponitirile, the quantitative relationship between the two substances may be selected freely. However, if the fact that the interchange reaction product is subsequently subjected to esterification is taken into consideration, the condition that the adiponitrile is in excess is preferable. Thus, usually 1-100 moles, preferably 1-70 moles and more preferably 1-50 moles of adiponitrile is employed per mole of adipic acid. The use of more than 100 moles of adiponitrile has no particular merit, only necessitating to enlarge the apparatus for reaction.

The temperature for the interchange reaction is usually 100° C. or higher, preferably 150°-270° C., and more preferably 200°-250° C. If the temperature is lower than 100° C., the reaction velocity is low. The use of a temperature higher than 270° C. has no merit, only making the reaction conditions severe. Although the reaction time may be varied depending on the quantitative relationship between adipic acid and adiponitrile used and on the reaction temperature, it is usually 0.1-20 hours, preferably 0.5-10 hours, and more preferably 1-5 hours.

Figure 1:
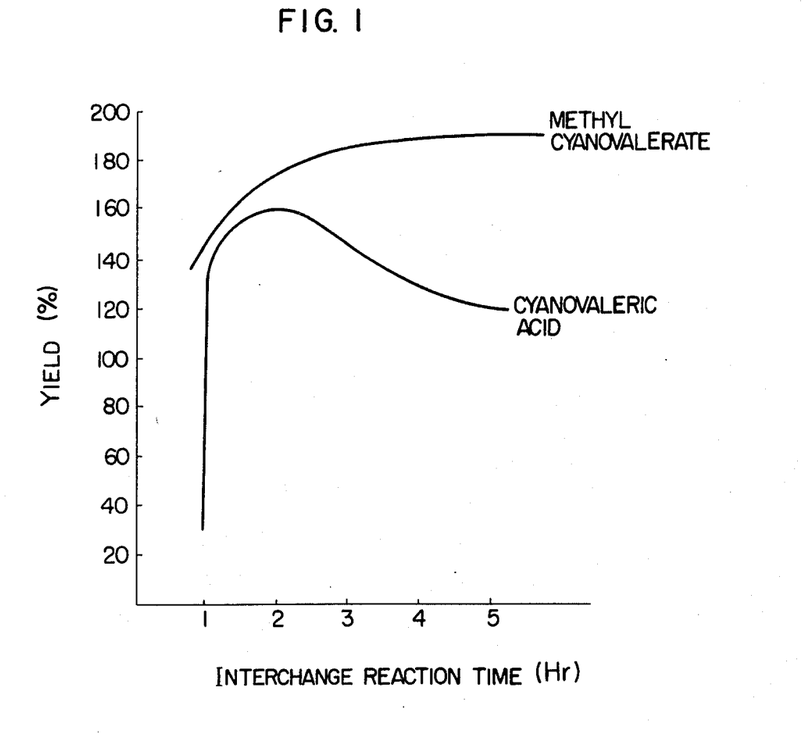
FIG. 1 is a graph illustrating the yields of cyanovaleric acid and methyl cyanovalerate in the interchange reaction between adipic acid and adiponitrile as a function of time.

In producing a cyanovaleric ester by esterifying the interchange reaction mixture with an alcohol, it is indispensable to carry out the esterification by directly adding the alcohol to the interchange reaction mixture without isolating the cyanovaleric acid formed by the interchange reaction. The reason therefor will be explained with reference to the accompanying drawings. FIG. 1 illustrates the yield of cyanovaleric acid formed by heating 1 mole of adipic acid and 10 moles of adiponitrile at 230° C. for a reaction time as shown in FIG. 1, where the yield of cyanovaleric acid is expressed by the following equation:

$$\text{Yield of cyanovaleric acid} = \frac{\text{Cyanovaleric acid formed (mole)}}{\text{Adipic acid (mole) used in the interchange reaction}} \times 100$$

and the yield of methyl cyanovalerate formed by adding methanol to the interchange reaction mixture and esterifying the cyanovaleric acid at 200° C. for 2 hours, where the yield of methyl cyanovalerate is expressed by the following equation:

$$\text{Yield of methyl cyanovalerate} = \frac{\text{Methyl cyanovalerate formed (mole)}}{\text{Adipic acid (mole) used in the interchange reaction}} \times 100$$

It is apparent from FIG. 1 that the yield of cyanovaleric acid formed by heating adipic acid and adiponitrile to allow the interchange reaction therebetween to proceed reaches a maximum value of about 160% and thereafter decreases with the lapse of time, but when methanol is directly added to the interchange reaction mixture according to the process of this invention to conduct the esterification methyl cyanovalerate can be obtained in an yield of about 190%.

It is impossible to allow the interchange reaction and the esterification to proceed simultaneously, because the esterification of adipic acid proceeds preferentially.

The alcohol used for esterifying the interchange reaction mixture may be any primary alcohol, and there may be used methanol, ethanol, n-propanol, i-propanol, n-butanol, sec-butanol, t-butanol and the like, among which methanol and ethanol are particularly preferable from the viewpoint of ease to separate the formed cyanovaleric ester from adiponitrile by distillation.

The amount of the alcohol used for esterifying the interchange reaction mixture is at least 2 moles per mole of the adipic acid used for the interchange reaction. Usually, the alcohol is used in an amount of 2-400 moles, preferably 2-200 moles and more preferably 2-100 moles, per mole of adipic acid. The use of more than 400 moles of the alcohol is impractical, only necessitating to enlarge the apparatus of reaction. The reaction temperature is usually 70°–350° C., preferably 100°–300° C., more preferably 150°–230° C. If the reaction temperature is lower than 70° C., the reaction velocity is too low. The use of a reaction temperature higher than 300° C. has no merit, only causing an elevation of reaction pressure. The reaction time is usually 0.5–20 hours, preferably 1–10 hours.

In the interchange reaction of this invention, it is also possible to use a monoester of adipic acid in place of the adipic acid. The liquid distillation residue obtained by separating the formed cyanovaleric ester from the reaction mixture by distillation can, of course, be used again as adiponitrile for interchange reaction. Thus, by adding to the distillation residue fresh adipic acid and adiponitrile in amounts equal to the amounts of those converted to the cyanovaleric ester and subjecting the resulting mixture to interchange reaction, a cyanovaleric ester can be obtained in a yield of about 200% based on the adipic acid freshly added.

The diester of adipic acid formed as a by-product by the esterification may be taken out of the system, or may be reused by recycling it to the interchange reaction system. The fact that the diester can be recycled and reused is particularly advantageous for the process of this invention providing a process for producing caprolactam without forming by-products.

The details of the second step of this invention for reducing the cyanovaleric ester obtained in the first step by the use of a catalyst to produce an aminocaproic ester will be mentioned below.

In general, nickel, palladium, platinum, rhodium, cobalt and the like are used as the catalyst for reducing nitriles to primary amines. Preferably, Raney catalysts, i.e. Raney nickel and Raney cobalt, are used for this purpose, among which Raney cobalt is more preferable. In reducing the cyanovaleric ester with Raney cobalt as the catalyst, it is also possible to use ammonia as a promotor.

In the reduction reaction, the Raney cobalt may be used in any proportion to the cyanovaleric ester. The reaction temperature is usually 20°–100° C., preferably 40°–80° C. If the reaction temperature is lower than 20° C., the reaction velocity is too low. If the reaction temperature is higher than 100° C., side reactions take place markedly and the yield of the main product decreases. The reaction pressure, expressed in terms of hydrogen pressure, is 5–100 kg/cm$^2$, preferably 10–50 kg/cm$^2$. If the pressure is lower than 5 kg/cm$^2$, the reaction velocity is too low. The use of a hydrogen pressure higher than 100 kg/cm$^2$ has no merit as to yield and reaction velocity, only a reaction vessel resistant to higher pressure is required. As the solvent, the alcohol for esterifying the interchange reaction mixture, as well as an ether, a dioxane and the like, may be used. It is also possible to carry out the reaction in the absence of the solvent. The reaction can be carried out batchwise or continuously. In the continuous process, it follows that the major part of the aminocaproic ester obtained is recycled again to the reaction system after the hydrogenation to reduce the cyanovaleric ester in a large excess of the aminocaproic ester.

The details of the third step of this invention for heating the aminocaproic ester obtained in the second step in a polyhydric alcohol having a boiling point higher than that of caprolactam to produce caprolactam are as follows:

The reason why a polyhydric alcohol having a boiling point higher than that of caprolactam is used is that after heating the aminocaproic ester in a polyhydric alcohol having a boiling point higher than that of caprolactam to convert the ester into caprolactam, the caprolactam produced is separated by distillation to allow the unconverted substances to be present in the liquid distillation residue in the state that they are diluted with the polyhydric alcohol having a boiling point higher than that of caprolactam, whereby when the liquid distillation residue is returned to the system for heating the aminocaproic ester, the unconverted substances can be converted to caprolactam, so that caprolactam can be obtained substantially quantitatively from the aminocaproic ester. As a matter of course, the unconverted substances can be converted into caprolactam also by heating said liquid distillation residue alone.

Thus, the polyhydric alcohol having a boiling point higher than that of caprolactam referred to in this invention may be any one having a boiling point difference from that of caprolactam enough to separate caprolactam by distillation and to allow the polyhydric alcohol containing the unconverted substances to be present as the distillation residue. As said polyhydric alcohol, there may be used, for example, triethylene glycol, tetraethylene glycol, polypropylene glycol, batyl alcohol, glycerin, diglycerin, pentaerythritol, 1,2,3-butanetriol, 2,3,4-pentanetriol and the like.

If a compound having a boiling point higher than that of caprolactam other than the polyhydric alcohol, such as a hydrocarbon, a monohydric alcohol or the like, is used as the solvent, an insoluble polymer is formed. If a compound having a boiling point lower than that of caprolactam is used as the solvent, the unconverted substances are denatured by polymerization or the like in the course of the removal of the solvent by distillation and subsequent separation of caprolactam by distillation, so that the conversion of the unconverted substances into caprolactam becomes impossible.

The temperature at which the aminocaproic ester is heated and reacted is usually 80°–300° C., preferably 100°–280° C. and more preferably 180°–250° C. The use of a temperature higher than 300° C. has no merit in respect of yield, only making the reaction condition severe. The reaction time is usually 0.1–10 hours, preferably 0.5–5.0 hours.

The concentration of the aminocaproic ester used in the reaction is usually 0.5–30% by weight, preferably 3–20% by weight and more preferably 5–15% by weight. The use of a concentration higher than 30% by weight is undesirable because it causes formation of a large amount of an insoluble polymer.

The conversion of the aminocaproic ester into caprolactam by heating the former in the above-mentioned solvent is accompanied by a simultaneous formation of an alcohol. The reaction may be allowed to proceed while removing this alcohol, or while allowing the alcohol to stay in the system by using a closed type of reaction apparatus.

Even when aminocaproic acid is substituted for the aminocaproic ester, caprolactam can be obtained in the same manner.

As above, the process of this invention is entirely different from the prior art techniques for the production of caprolactam in that it provides a process for producing caprolactam in a high yield by using adipic acid and adiponitrile as starting materials and without forming by-product at all, so that its practical value is very high.

The process of this invention for producing caprolactam from adipic acid and adiponitrile will be illustrated below with reference to FIG. 2 of the accompanying drawings and based on the preferable embodiment, by dividing it into the following three steps: the first step of producing methyl cyanovalerate, the second step of producing methyl aminocaproate and the third step of producing caprolactam.

Figure 2:
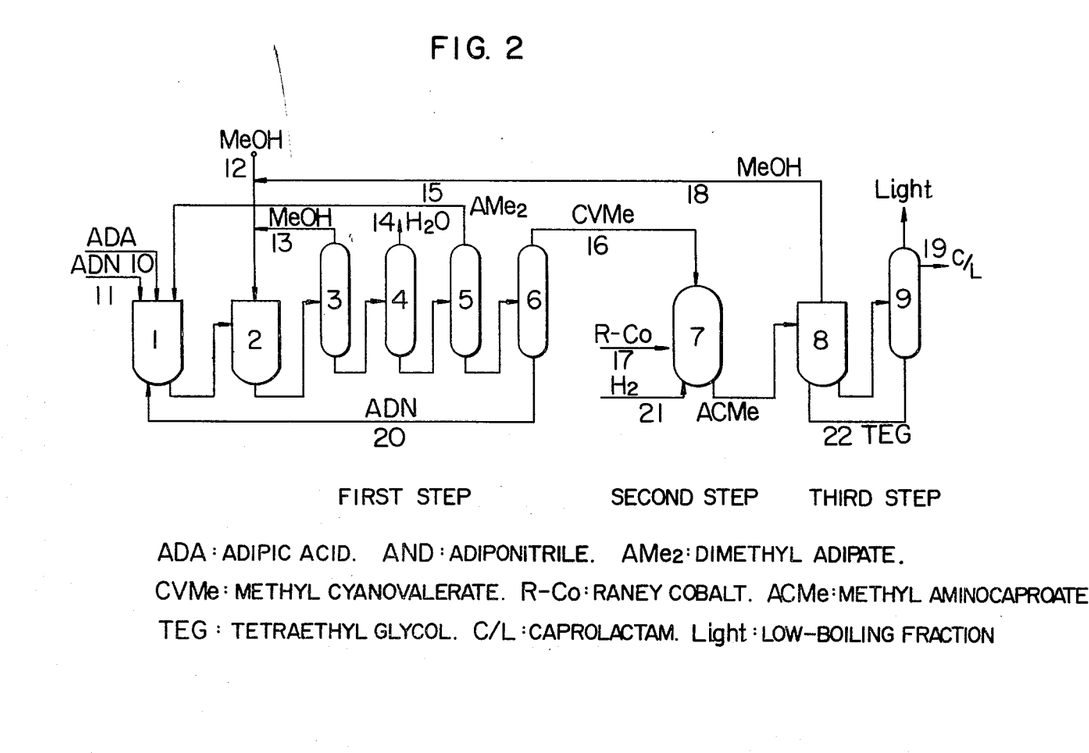
FIG. 2 is a flow sheet illustrating one example of the process for producing caprolactam from adipic acid and adiponitrile.

FIG. 2 is a flow sheet illustrating one example of the process for producing caprolactam from adipic acid and adiponitrile by esterifying the interchange reaction mixture between adipic acid and adiponitrile with methanol, carrying out the reduction of the methyl cyanovalerate continuously in the absence of a solvent and converting the methyl aminocaproate into caprolactam by heating the former while removing methanol.

In the first step of producing methyl cyanovalerate, 1 is an interchange reactor, to which adipic acid and adiponitrile are sent via conduits 10 and 11, respectively, and the dimethyl adipate and adiponitrile withdrawn from distillation towers 5 and 6 are recycled. The interchange reaction between adipic acid and adiponitrile progresses in the interchange reactor 1, and the reaction mixture is sent directly to an estreification reactor 2 under pressure without being subjected to any operation such as separation or the like, and methanol is recycled to the reactor 1 from a distillation tower 3 and a cyclization reactor 8. The liquid reaction mixture containing methyl cyanovalerate formed in the esterification reactor 2 under pressure is sent to the methanol-removing tower 3, namely the distillation tower 3, a dehydration tower 4 and the dimethyl adipate-removing tower 5, namely the distillation tower 5, successively, and methanol, water and dimethyl adipate are removed by distillation in the respective towers, after which the liquid residual reaction mixture is sent to the distillation tower 6. The methanol distilled out is recycled to the esterification reactor 2 via a conduit 13. The water distilled out is withdrawn out of the system via a conduit 14. The dimethyl adipate distilled out is recycled to the interchange reactor 1 via a conduit 15. In the distillation tower 6, methyl cyanovalerate is distilled. The methyl cyanovalerate distilled out is sent to a hydrogenation reactor 7, while the liquid distillation residue composed mainly of adiponitrile is withdrawn from the lower part of the distillation tower 6 and sent to the interchange reactor 1 via a conduit 20.

In the second step of producing methyl aminocaproate, the methyl cyanovalerate sent from the distillation tower 6 via a conduit 16 is contacted in a hydrogenation reactor 7 with the Raney cobalt supplied from a conduit 17 and the hydrogen supplied from a conduit 21, whereby it is reduced to methyl aminocaproate. The reaction mixture is sent to a cyclization reactor 8.

In the third step of producing caprolactam, the methyl aminocaproate sent from the hydrogenation reactor 7 is heated in the cyclization reactor 8 together with the polyhydric alcohol having a boiling point higher than that of caprolactam supplied from a distillation tower 9, whereby caprolactam is produced.

The polyhydric alcohol having a boiling point higher than that of caprolactam, containing caprolactam, is sent to the distillation tower 9, where caprolactam is withdrawn from the upper part, and the polyhydric alcohol having a boiling point higher than that of caprolactam, containing the unconverted substances, is recycled to the cyclization reactor 8 via a conduit 22. In the cyclization reactor 8, it is heated together with newly supplied methyl aminocaproate, to be converted into caprolactam.

This invention will be illustrated below in more detail referring to Examples which are not by way of limitation but by way of illustration.

EXAMPLE 1

In the first place, the following starting solutions A and B were prepared.

Solution A

Into a 1-liter, stainless autoclave were introduced 43.8 g (0.300 mole) of adipic acid, 52.2 g (0.300 mole) of dimethyl adipate and 324.0 g (3.000 moles) of adiponitrile. After purging with nitrogen, the content was stirred at 230° C. for 2.5 hours. The analysis by a high performance liquid chromatography revealed that 58.6 g of cyanovaleric acid had been formed. After cooling the reaction mixture, 160.0 g (5.000 moles) of methanol was added and stirred at 200° C. for 2 hours. After completion of the esterification, the reaction mixture was analysed by a gas chromatography to find the formation of 76.1 g (0.540 mole) of methyl cyanovalerate and 51.8 g (0.298 mole) of dimethyl adipate. The methanol, water, dimethyl adipate and methyl cyanovalerate were separated from the liquid reaction mixture by distillation in the usual manner to obtain 301.2 g of the liquid distillation residue. Hereinafter, this liquid distillation residue is referred to as Solution A.

Solution B

Into a 2-liter, stainless autoclave were introduced 82.4 g (0.568 mole) of methyl aminocaproate and 741.6 g of tetraethylene glycol. After purging with nitrogen, the content was stirred at 230° C. for 1 hour. After completion of the reaction, the reaction mixture was distilled under reduced pressure to remove methanol and 56.5 g (0.500 mole) of caprolactam, thereby obtaining 749.3 g of the liquid distillation residue. Hereinafter, this liquid distillation residue is referred to as "Solution B".

Into a 1-liter, stainless autoclave were introduced 301.2 g of Solution A, 39.4 g (0.270 mole) of adipic acid, 51.8 g (0.298 mole) of dimethyl adipate and 29.2 g (0.270 mole) of adiponitrile. The content of the autoclave was stirred at 230° C. for 2.5 hours. After cooling the reaction mixture, 160.0 g of methanol was added and the resulting mixture was stirred at 200° C. for 2 hours. Then, the liquid reaction mixture was distilled under reduced pressure to obtain 77.5 g (0.550 mole) of methyl cyanovalerate. The yield thereof corresponded to 203.7% based on the adipic acid charged.

Then, 70.5 g (0.500 mole) of methyl cyanovalerate and a methanolic slurry of Raney cobalt (trade name of Kawaken Fine Chemical K. K.; OF) was developed in a conventional manner (said slurry consisting of 20.0 g of Raney cobalt and 20.0 g of methanol) were introduced into a 300-ml, stainless autoclave. After purging with nitrogen, reaction was carried out at a hydrogen pressure of 30 kg/cm² at a reaction temperature of 60° C. while supplying hydrogen so as to maintain the hydrogen pressure at 30 kg/cm², until the absorption of hydrogen ceased. After completion of the reaction, the liquid reaction mixture was analyzed by a gas chromatography to confirm the formation of 69.6 g (0.480 mole) of methyl aminocaproate and 1.9 g (0.017 mole) of caprolactam. The total yield of methyl aminocaproate and caprolactam was 99.4%. This liquid reaction mixture was introduced into a 2-liter, stainless autoclave while washing the catalyst with methanol, after which 749.3 g of Solution B was added and the methanol was removed by distillation under reduced pressure at room temperature. Subsequently, the autoclave was purged with nitrogen, and the content of the autoclave was then stirred at 230° C. for 1 hour. The liquid reaction mixture was analyzed by a gas chromatography to confirm the formation of 56.4 g (0.499 mole) of caprolactam. The yield thereof corresponded to 99.8% based on the methyl cyanovalerate used in the reduction reaction, indicating that substances not confirmed as reduction products could also be converted into caprolactam.

COMPARATIVE EXAMPLE 1

In the same manner as in Example 1, 70.5 g (0.500 mole) of methyl cyanovalerate was reduced to obtain a liquid reaction mixture comprising 69.8 g of methyl aminocaproate and 1.9 g of caprolactam. The reaction mixture was introduced into a 2-liter, stainless autoclave together with 652.5 g of ethyleneglycol. After distilling off the methanol under reduced pressure at room temperature, the inner pressure was returned to ordinary pressure by introducing nitrogen, after which the content of the autoclave was stirred at 230° C. for 1 hour. Analysis of the liquid reaction mixture clarified the formation of 49.1 g (0.435 mole) of caprolactam.

Then, the liquid reaction mixture was distilled, whereby methanol, ethyleneglycol and 48.2 g (0.427 mole) of caprolactam were distilled off. No caprolactam was detected in the distillation residue. The distillation residue, the reaction mixture obtained by reducing 60.2 g (0.427 mole) of methyl cyanovalerate, and 652.5 g of ethyleneglycol were introduced into a 2-liter, stainless autoclave, and treated in the same manner as above. The reaction mixture was analyzed to confirm the formation of 42.5 g (0.376 mole) of caprolactam. The yield of caprolactam corresponded to 88.1% based on the newly added methyl cyanovalerate.

EXAMPLE 2

In place of Solution B used in Example 1, there was used the whole quantity of the liquid distillation residue obtained in Example 1 by removing, by distillation, methanol and 56.1 g (0.496 mole) of caprolactam from the caprolactam-containing tetraethyleneglycol solution (no caprolactam was detected in said liquid distillation residue by a gas chromatography). Thus, said liquid distillation residue was introduced into a 2-liter, stainless autoclave together with the liquid reaction mixture obtained by reducing 69.9 g (0.496 mole) of methyl cyanovalerate in the same manner as in Example 1, after which the reaction was carried out in the same manner as in Example 1. The reaction mixture was analyzed to confirm the existence of 56.3 g (0.498 mole) of caprolactam. The yield of caprolactam corresponded to 100.4% based on the methyl cyanovalerate newly used in the reaction. Hereinafter, this experiment is referred to as Repeated Experiment 1.

Then, by the same procedure as above, the reaction mixture obtained by reducing methyl cyanovalerate in an amount equimolar to the caprolactam distilled off was successively added to the distillation residue obtained in the foregoing run, and the reaction and distillation were repeated. Hereinafter, these experiments are referred to as Repeated Experiments 2-6. The results are shown in Table 1.

TABLE 1

| Repeated Experiment No. | Caprolactam formed in the foregoing Repeated Experiment (mole) | Caprolactam distilled off in the foregoing Repeated Experiment (mole) | Methyl cyanovalerate used for reduction (mole) | Caprolactam formed (mole) | Yield $\frac{\text{Caprolactam formed}}{\text{Methyl cyanovalerate used for reduction}} \times 100$ |
|---|---|---|---|---|---|
| 2 | 0.498 | 0.494 | 0.494 | 0.492 | 99.6 |
| 3 | 0.492 | 0.487 | 0.487 | 0.480 | 98.6 |
| 4 | 0.480 | 0.476 | 0.476 | 0.484 | 101.7 |
| 5 | 0.484 | 0.484 | 0.484 | 0.485 | 100.2 |
| 6 | 0.485 | 0.484 | 0.484 | 0.481 | 99.4 |

EXAMPLE 3

Into a 1-liter, stainless autoclave were introduced 29.2 g (0.200 mole) of adipic acid and 324.0 g (3.000 moles) of adiponitrile. After purging with nitrogen, the content was stirred at 240° C. for 3 hours. The analysis by a high performance liquid chromatography revealed that 11.5 g of cyanovaleric acid had been formed. After cooling the reaction mixture, 138.0 g (3.000 moles) of ethanol was added and stirred at 190° C. for 3 hours. After completion of the esterification, the reaction mixture was analyzed by a gas chromatography to confirm the formation of 60.1 g (0.388 mole) of ethyl cyanovalerate and 1.0 g (0.005 mole) of diethyl adipate. The reaction mixture was distilled in the usual manner to remove ethanol, water, diethyl adipate and ethyl cyanovalerate.

Then, 29.1 g (0.199 mole) of adipic acid and 21.0 g (0.194 mole) of adiponitrile were added to the liquid distillation residue, and the resulting mixture was introduced into a 1-liter, stainless autoclave. after purging with nitrogen, the content was stirred at 240° C. for 3 hours. After cooling the reaction mixture, 138.0 g (3.000 moles) of ethanol was added and the resulting mixture was stirred at 190° C. for 3 hours. As a result of analysis, it was confirmed that 60.3 g (0.389 mole) of ethyl cyanovalerate and 1.2 g (0.006 mole) of diethyl adipate were formed.

A 108.5-g (0.700-mole) portion of the ethyl cyanovalerate obtained in the above-mentioned two runs of reaction was introduced into a 1-liter autoclave together with an ethanolic slurry of Raney cobalt (consisting of 21.7 g of Raney cobalt and 60.0 g of ethanol) and 374.0 g of ethanol. After purging with nitrogen, reaction was carried out at a hydrogen pressure of 60 kg/cm$^2$ at a reaction temperature of 45° C. while supplying hydrogen so as to maintain the hydrogen pressure at 60 kg/cm$^2$, until the absorption of hydrogen ceased. After completion of the reaction, the reaction mixture was analyzed by a gas chromatography to confirm the formation of 109.4 g (0.688 mole) of ethyl aminocaproate and 1.1 g (0.010 mole) of caprolactam (the total yield of ethyl aminocaproate and caprolactam was 99.7%). The catalyst was separated from the reaction mixture and washed with ethanol, after which the washings were added to the reaction mixture to obtain 700.0 g of an ethanolic solution. A 100.0-g portion of this ethanolic solution (0.100 mole as ethyl cyanovalerate used for the reduction) and 90.0 g of diglycerin were introduced into a 300-ml, three-necked flask, the ethanol was distilled off by elevating the inner temperature to 80° C., after which the content of the flask was stirred at 200° C. for 4 hours while distilling off the ethanol. After completion of the reaction, the reaction mixture was distilled under reduced pressure to obtain 9.3 g (0.082 mole) of caprolactam. The yield thereof corresponded to 82.0% based on the ethyl cyanovalerate used for the reduction. (Hereinafter, in this Example, the yield of caprolactam is based on ethyl cyanovalerate.)

Subsequently, 82.0 g of the above-mentioned ethanolic solution of ethyl aminocaproate (0.082 mole as ethyl cyanovalerate used for the reduction) was added to the liquid distillation residue, and the reaction and distillation were carried out under the same conditions as above to obtain 9.2 g (0.081 mole) of caprolcatam. The yield of caprolactam corresponded to 99.8% based on the ethyl cyanovaerate from which the newly added ethyl aminocaproate had been formed (Repeated Experiment 1). Subsequently, in the same manner as above, an ethanolic solution obtained by reducing ethyl cyanovalerate in an amount equimolar to the caprolactam distilled off was successively added to the foregoing liquid distillation residue, and the reaction and distillation were repeated (Repeated Experiments 2-5). The results are shown in Table 2.

EXAMPLES 4-6

Reaction was carried out in the same manner as in Example 3, except that the diglycerin used as the solvent in Example 3 was replaced by tetraethyleneglycol in Example 4, by pentaerythritol in Example 5 and by 1,2,3-butanetriol in Example 6. The results are shown in Table 2. The yield of caprolcatam is based on ethyl cyanovalerate as in Example 3.

TABLE 2

| Example No. | Example 3 | Example 4 | Example 5 | Example 6 |
|---|---|---|---|---|
| The first run of reaction | 82.0 | 83.4 | 79.8 | 81.9 |
| Repeated Experiment 1 | 98.8 | 101.1 | 98.8 | 99.2 |
| Repeated Experiment 2 | 99.2 | 97.2 | 96.2 | 99.6 |
| Repeated Experiment 3 | 99.2 | 100.6 | 99.9 | 98.2 |
| Repeated Experiment 4 | 100.1 | 98.5 | 100.0 | 99.0 |
| Repeated Experiment 5 | 99.8 | 99.0 | 99.8 | 100.7 |

TABLE 2-continued

| Example No. | Example 3 | Example 4 | Example 5 | Example 6 |
|---|---|---|---|---|
| Experiment 5 | | | | |

EXAMPLE 7

Into a 2-liter, stainless autoclave were introduced 73.0 g (0.500 mole) of adipic acid, 432.0 g (4.000 moles) of adiponitrile and 26.1 g (0.150 mole) of dimethyl adipate. After purging with nitrogen, the content was stirred at 220° C. for 5 hours. After cooling the reaction mixture 320.0 g (10.000 moles) of methanol was added and the resulting mixture was stirred at 220° C. for 1 hour. By distilling the reaction mixture, there were obtained 114.2 g (0.810 mole) of methyl cyanovalerate and 26.8 g (0.154 mole) of dimethyl adipate.

Then, 59.1 g (0.405 mole) of adipic acid, 43.7 g (0.405 mole) of adiponitrile and 26.8 g (0.154 mole) of dimethyl adipate were added to the liquid distillation residue and the resulting mixture was introduced into the autoclave mentioned above. Thereafter, reaction was carried out in the same manner as above. As a result of distillation, there were obtained 120.0 g (0.851 mole) of methyl cyanovalerate and 25.6 g (0.147 mole) of dimethyl adipate (Repeated Experiment 1). Subsequently, by the same procedure as above, the same amount of adipic acid as used in Repeated Experiment 1 and adiponitrile in an amount as shown in Table 3 were added to the liquid distillation residue obtained by distilling off methyl cyanovalerate and dimethyl adipate, and the reaction and distillation were repeated (Repeated Experiments 2-5). The results are shown in Table 3.

TABLE 3

| | Composition of charge (g-mole) | | | Amount of product obtained by distillation (g-mole) | |
|---|---|---|---|---|---|
| Repeated Experiment No. | Adipic acid | Dimethyl adipate | Adiponitrile | Methyl cyanovalerate | Dimethyl adipate |
| 1 | 59.1–0.405 | 26.8–0.154 | 43.7–0.405 | 20.0–0.851 | 25.6–0.147 |
| 2 | 59.1–0.405 | 25.6–0.147 | 48.2–0.446 | 122.4–0.868 | 24.6–0.141 |
| 3 | 59.1–0.405 | 24.6–0.141 | 50.0–0.463 | 128.3–0.910 | 27.8–0.160 |
| 4 | 59.1–0.405 | 27.8–0.160 | 54.5–0.505 | 134.2–0.952 | 26.1–0.150 |
| 5 | 59.1–0.405 | 26.1–0.150 | 59.1–0.547 | 126.1–0.894 | 26.3–0.151 |

A 141.0-g (1.000-mole) portion of the methyl cyanovalerate thus obtained was introduced into a 500-ml stainless autoclave together with a methanolic slurry of Raney cobalt consisting of 14.1 g of Raney cobalt and 40.0 g of methanol. After completely distilling off the methanol at room temperature under reduced pressure, the inner pressure was returned to ordinary pressure by introducing nitrogen, and then the autoclave was additionally two times purged with nitrogen, after which reaction was carried out at a hydrogen pressure of 20 kg/cm$^2$ at a reaction temperature of 80° C. while supplying hydrogen so as to maintain the hydrogen pressure at 20 kg/cm$^2$ until the absorption of hydrogen ceased. The catalyst was removed from the reaction mixture by filtration and washed with methanol, and the methanolic washings were added to the reaction mixture to obtain 200.0 g of a mixed solution. The solution was analyzed by a gas chromatography to confirm the formation of 125.0 g (0.862 mole) of methyl aminocaproate and 15.3 g (0.135 mole) of caprolactam.

Then, 100.0 g of the reduction reaction mixture was introduced into a 1-liter, three-necked flask together with 480.0 g of triethyleneglycol, and the methanol was distilled off by elevating the inner temperature to 70° C. Then, the content of the flask was stirred at 250° C. for 1 hour while distilling off the methanol. After completion of the reaction, the reaction mixture was distilled under reduced pressure to obtain 50.9 g (0.450 mole) of caprolactam. The yield of caprolactam corresponded to 90.0% based on the methyl cyanovalerate. Then, 90.0 g of the reduction reaction mixture was added to the liquid distillation residue, after which reaction was carried out in the same manner as above and the product was distilled under reduced pressure. As a result, 50.9 g (0.450 mole) of caprolactam was obtained. The yield of caprolactam corresponded to 100.0% based on the methyl cyanovalerate newly added to the reduction reaction mixture.

EXAMPLE 8

By repeating the procedure of Example 7, 141.0 g of methyl cyanovalerate was obtained. Subsequently, it was reduced under the conditions shown in Table 4 (Experiment Nos. 1-5). The results are shown in Table 4.

TABLE 4

| Experiment No. | Composition of charge | | | Yield of the reacton product (%) | | |
|---|---|---|---|---|---|---|
| | Methyl cyano-valerate (g) | Raney cobalt (g) | Solvent (g) | Methyl amino-caproate | Caprolactam | Total yield |
| 1 | 28.2 | 2.8 | Ethyl ether 100.0 | 96.1 | 3.2 | 99.3 |
| 2 | 28.2 | 2.8 | Dioxane 100.0 | 97.0 | 2.4 | 99.4 |
| 3 | 28.2 | 2.8 | Methanol 100.0 | 96.3 | 3.6 | 99.9 |
| 4 | 28.2 | 2.8 | Methanol 60.0 | 95.8 | 3.7 | 99.5 |
| 5 | 28.2 | 2.8 | — | 94.1 | 5.1 | 99.2 |

Note:
Hydrogen pressure 30 kg/cm$^2$
Reaction temperature 40° C.

Subsequently, the reaction mixture obtained in Experiment No. 1 and 500.0 g of tetraethylene glycol were introduced into a 1-liter stainless autoclave. After completely distilling off the solvent at room temperature under reduced pressure and purging the autoclave with nitrogen, the content of the autoclave was stirred at 210° C. for 5 hours. After completion of the reaction, distillation was carried out under reduced pressure to obtain 18.1 g (0.160 mole) of caprolactam.

Then, a hydrogenated solution (a solution prepared by mixing together the hydrogenated solutions of Hydrogenation Experiments Nos. 2-5 and then dividing the mixture into five equal portions) was added to the liquid distillation residue. After distilling off the solvent, the reaction and distillation were repeated in the same manner as above. As a result, caprolactam was obtained in yields of 99.6%, 101.4%, 97.2%, 98.1% and 100.8%.

What is claimed is:

1. A liquid phase process for producing caprolactam which comprises subjecting adipic acid and adiponitrile to interchange reaction at an elevated temperature, adding at least two moles of a lower alkanol per mole of adipic acid directly to the reaction mixture without isolating the resulting cyanovaleric acid to thereby esterify the cyanovaleric acid with said lower alkanol into a cyanovaleric ester, reducing the cyanovaleric ester with a reduction catalyst into the corresponding aminocaproic ester, heating at 80°-300° C. said aminocaproic ester in an amount of 0.5-30% by weight in a polyhydric alcohol having a higher boiling point than that of caprolactam, and isolating the caprolactam by distillation.

2. A process according to claim 1, wherein the molar ratio between adipic acid and adiponitrile is selected from the range of 1 : 1 to 1 : 50.

3. A process according to claim 1, wherein said lower alkanol is methanol or ethanol.

4. A process according to claim 1, wherein said lower alkanol is added in an amount of 1-50 moles per mole of the free carboxyl group of the adipic acid.

5. A process according to claim 1, wherein the temperature at which said lower alkanol is added and reacted is 150°-230° C.

6. A process according to claim 1, wherein the distillation residue obtained by distilling the esterification mixture to remove the cyanovaleric ester is recycled to the reaction system for the reaction of adipic acid and adiponitrile.

7. A process according to claim 1, wherein the concentration of said aminocaproic ester in the polydric alcohol is 3-20% by weight.

8. A process according to claim 1, wherein the temperature for heating and reaction of the aminocaproic acid ester is 130°-250° C.

9. A process according to claim 1, wherein said aminocaproic ester is methyl aminocaproate or ethyl aminocaproate.

10. A process according to claim 1, wherein said polyhydric alcohol is tetraethylene glycol.

11. A process according to claim 1, wherein the liquid distillation residue is recycled to the system for heating said polyhydric alcohol and said amino caproic ester.

12. A process according to claim 1, wherein the interchange reaction is conducted at 100° C. or higher.

* * * * *

UNITED STATES PATENT AND TRADEMARK OFFICE
CERTIFICATE OF CORRECTION

PATENT NO. : 4,470,928
DATED : September 11, 1984
INVENTOR(S) : KOHJI KIMURA ET AL It is certified that error appears in the above-identified patent and that said Letters Patent is hereby corrected as shown below:

On the cover page, Item [30], change "164567" to --- 56-164567 ---.

On the cover page, Item [30], change "194376" to --- 56-194376 ---.

Signed and Sealed this

Sixteenth Day of July 1985

[SEAL]

Attest:

DONALD J. QUIGG

Attesting Officer       Acting Commissioner of Patents and Trademarks